(12) United States Patent
Isak et al.

(10) Patent No.: US 6,737,544 B1
(45) Date of Patent: May 18, 2004

(54) METHOD FOR DRYING PHENOXYMETHYLBENZOIC ACIDS

(75) Inventors: Heinz Isak, Böhl-Iggelheim (DE); Martin Lambert, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/787,613

(22) PCT Filed: Oct. 15, 1999

(86) PCT No.: PCT/EP99/07826

§ 371 (c)(1), (2), (4) Date: Mar. 20, 2001

(87) PCT Pub. No.: WO00/23413

PCT Pub. Date: Apr. 27, 2000

(30) Foreign Application Priority Data

Oct. 20, 1998 (DE) .......................... 198 48 200

(51) Int. Cl.⁷ .............................. C07C 65/00
(52) U.S. Cl. ...................................... 562/473
(58) Field of Search ........................ 562/473

(56) References Cited

U.S. PATENT DOCUMENTS 3,420,851 A * 1/1969 Bloom et al. ................ 260/333
5,221,762 A   6/1993 Wingert et al. .............. 560/35

FOREIGN PATENT DOCUMENTS

| EP | 0 712 833 | | 5/1996 |
| EP | 0 937 702 | | 8/1999 |
| GB |   950717  | * | 3/1910 |
| GB |   773594  | * | 5/1957 |
| WO | WO98/14420 | | 4/1998 |

OTHER PUBLICATIONS

Van Nostrand's Scientific Encyclopedia, 7$^{th}$ ed. Considine and Considine, editors. pp. 939–943 (1989).*
The Organic Chem Lab Survival Manual—A Student's Guide to Techniques 4$^{th}$ ed. James W. Zubrick "The Melting Point Experiment" pp. 102–119, John Wiley & Sons (1997).*

* cited by examiner

Primary Examiner—Richard L. Raymond
Assistant Examiner—Zachary C. Tucker
(74) Attorney, Agent, or Firm—Keil & Weinkauf

(57) ABSTRACT

A process for drying phenoxymethylbenzoic acids of the general formula I

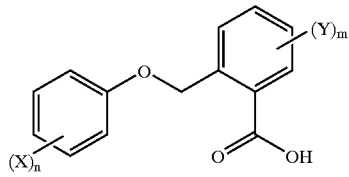

where X, Y, m and n have the following meanings:
 X, Y halogen or a C-organic radical,
 m a value from 0 to 4 and
 n a value from 0 to 5
which comprises drying the water- and/or solvent-wet phenoxymethylbenzoic acids at a temperature in the range from 1° to 25° C. above their melting point under the reaction conditions used.

4 Claims, No Drawings

METHOD FOR DRYING PHENOXYMETHYLBENZOIC ACIDS

The present invention relates to a process for drying phenoxymethylbenzoic acids of the general formula I

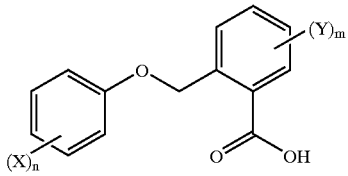

where X, Y, m and n have the following meanings:
X, Y halogen or a C-organic radical,
m a value from 0 to 4 and
n a value from 0 to 5.

Phenoxymethylbenzoic acids of the formula I are valuable intermediates for preparing fungicidal active substances.

DE 27 49 957 describes a process for preparing inter alia compounds of the formula I from phthalide and phenol derivatives. However, the yields are unsatisfactory, and the resulting products are prone to agglutination and agglomeration after drying.

Distinctly higher yields are obtained in the process of EP-A 493 711, but the products obtainable thereby show poor flow characteristics, and consolidation occurs due to bridge formation. Industrial implementation of the process is thereby made difficult, because processing of the solid and transporting the wet and dry material, and storage thereof, are problematic. An additional factor is that explosive dust mixtures may be produced during drying. These problems make it necessary when carrying out the process to operate with considerable industrial complexity which has a distinctly adverse effect on the economics of the process as a whole.

It is an object of the present invention to provide a process for drying phenoxymethylbenzoic acids of the formula I which does not have the disadvantages described and provides, in a simple manner, a product which is easy to process further.

We have found that this object is achieved by a process as claimed in claim 1, where the drying of water- and/or solvent-wet phenoxymethylbenzoic acids is carried out in a liquid phase.

The phenoxymethylbenzoic acids have the general formula

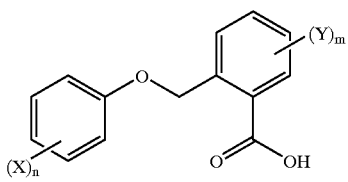

where X, Y, m and n have the following meanings:
X, Y halogen or a C-organic radical,
m a value from 0 to 4 and
n a value from 0 to 5.

Halogen can in this case be Cl, Br, I or F, preferably Cl or F.

The value of n and m is preferably in the range from 0 to 3, preferably 0 or 1.

C-organic radical is intended to mean in principle any radical which is to be assigned to the area of organic chemistry. The following may be mentioned here merely by way of example:

$C_1$–$C_6$-alkyl such as: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, n-propyl, 1-methylethyl, n-butyl, 1,1-dimethylethyl, n-pentyl or n-hexyl;

$C_1$–$C_6$-haloalkyl such as: a $C_1$–$C_6$-alkyl radical as mentioned above which is partially or completely substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

cyano-$C_1$–$C_6$-alkyl such as: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methyl-prop-3-yl, 2-cyano-2-methyl-prop-3-yl, 3-cyano-2-methyl-prop-3-yl or 2-cyanomethyl-prop-2-yl, in particular cyanomethyl or 2-cyanoethyl;

phenyl-$C_1$–$C_6$-alkyl such as: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)-eth-1-yl, 1-(phenylmethyl)-1-(methyl)-eth-1-yl or 1-(phenylmethyl)-prop-1-yl, in particular benzyl or 2-phenylethyl;

phenyl-($C_1$–$C_6$-alkyl)carbonyloxy such as: for example benzylcarbonyloxy, 1-phenylethylcarbonyloxy, 2-phenylethylcarbonyloxy, 1-phenylprop-1-ylcarbonyloxy, 2-phenylprop-1-ylcarbonyloxy, 3-phenylprop-1-ylcarbonyloxy, 1-phenylbut-1- ylcarbonyloxy, 2-phenylbut-1-ylcarbonyloxy, 3-phenylbut-1-ylcarbonyloxy, 4-phenylbut-1-ylcarbonyloxy, 1-phenylbut-2-ylcarbonyloxy, 2-phenylbut-2-ylcarbonyloxy, 3-phenylbut-2-ylcarbonyloxy, 4-phenylbut-2-ylcarbonyloxy, 1-(phenylmethyl)-eth-1-ylcarbonyloxy, 1-(phenylmethyl)-1-(methyl)-eth-1-ylcarbonyloxy or 1-(phenylmethyl)-prop-1-ylcarbonyloxy, in particular benzylcarbonyloxy or 2-phenylethylcarbonyloxy;

phenyl-$C_1$–$C_6$-alkylsulfonyloxy such as: for example benzylsulfonyloxy, 1-phenylethylsulfonyloxy, 2-phenylethylsulfonyloxy, 1-phenylprop-1-ylsulfonyloxy, 2-phenylprop-1-ylsulfonyloxy, 3-phenylprop-1-ylsulfonyloxy, 1-phenylbut-1-ylsulfonyloxy, 2-phenylbut-1-ylsulfonyloxy, 3-phenylbut-1-ylsulfonyloxy, 4-phenylbut-1-ylsulfonyloxy, 1-phenylbut-2-ylsulfonyloxy, 2-phenylbut-2-ylsulfonyloxy, 3-phenylbut-2-ylsulfonyloxy, 4-phenylbut-2-ylsulfonyloxy, 1-(phenylmethyl)-eth-1-ylsulfonyloxy, 1-(phenylmethyl)-1-(methyl)-eth-1-ylsulfonyloxy or 1-(phenylmethyl)-prop-1-ylsulfonyloxy, in particular benzylsulfonyloxy or 2-phenylethylsulfonyloxy;

($C_1$–$C_6$-alkyl)carbonyl such as: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-etbylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular methylcarbonyl, ethylcarbonyl or 1-methylethylcarbonyl;

($C_1$–$C_6$-alkyl)carbonyl-$C_1$–$C_6$-alkyl such as: $C_1$–$C_6$-alkyl which is substituted by ($C_1$–$C_6$-alkyl)carbonyl as mentioned above, i.e., for example, methylcarbonylmethyl;

($C_1$–$C_4$-alkyl)carboxyl such as: methylcarboxyl, ethylcarboxyl, n-propylcarboxyl, 1-methylethylcarboxyl, n-butylcarboxyl, 1-methylpropylcarboxyl, 2-methylpropylcarboxyl or 1,1-dimethylethylcarboxyl, in particular methylcarboxyl;

($C_1$–$C_6$-haloalkyl)carbonyl such as: a ($C_1$–$C_6$-alkyl)carbonyl radical as mentioned above which is partially or completely substituted by fluorine, chlorine, bromine and/or iodine, i.e., for example, chloroacetyl, dichloroacetyl, trichloroacetyl, fluoroacetyl, difluoroacetyl, is trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chlor-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl, nonafluorobutylcarbonyl, (5-fluoro-1-pentyl)carbonyl, (5-chloro-1-pentyl)carbonyl, (5-bromo-1-pentyl)carbonyl, (5-iodo-1-pentyl)carbonyl, (5,5,5-trichloro-1-pentyl)carbonyl, undecafluoropentylcarbonyl, (6-fluoro-1-hexyl)carbonyl, (6-chloro-1-hexyl)carbonyl, (6-bromo-1-hexyl)carbonyl, (6-iodo-1-hexyl)carbonyl, (6,6,6-trichloro-1-hexyl)carbonyl or dodecafluorohexylcarbonyl, in particular trifluoroacetyl;

($C_1$–$C_6$-alkyl)carbonyloxy such as: acetyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentylcarbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutyl-carbonyloxy, 2-ethylbutylcarbonyloxy, 1,1,2-trimethylpropylcarbonyloxy, 1,2,2-trimethylpropylcarbonyloxy, 1-ethyl-1-methylpropylcarbonyloxy or 1-ethyl-2-methylpropylcarbonyloxy, in particular acetyloxy;

($C_1$–$C_6$-haloalkyl)carbonyloxy such as: a ($C_1$–$C_6$-alkyl)-carbonyloxy radical as mentioned above which is partially or completely substituted by fluorine, chlorine, bromine and/or iodine, i.e., for example, chloroacetyloxy, dichloroacetyloxy, trichloroacetyloxy, fluoroacetyloxy, difluoroacetyloxy, trifluoroacetyloxy, chlorofluoroacetyloxy, dichlorofluoroacetyloxy, chlorodifluoroacetyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, pentafluoroethylcarbonyloxy, 2-fluoropropylcarbonyloxy, 3-fluoropropylcarbonyloxy, 2,2- difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, 2,2,3,3,3-pentafluoropropylcarbonyloxy, heptafluoropropylcarbonyloxy, 1-(fluoromethyl)-2-fluoroethylcarbonyloxy, 1-(chloromethyl)-2-chloroethylcarbonyloxy, 1-(bromomethyl)-2-bromoethylcarbonyloxy, 4-fluorobutylcarbonyloxy, 4-chlorobutylcarbonyloxy, 4-bromobutylcarbonyloxy or nonafluorobutylcarbonyloxy, in particular trifluoroacetoxy;

($C_1$–$C_6$-alkyl)carbonyloxy-$C_1$–$C_6$-alkyl such as: $C_1$–$C_6$-alkyl which is substituted by ($C_1$–$C_6$-alkyl) carbonyloxy as mentioned above, i.e., for example, methylcarbonyloxymethyl, ethylcarbonyloxymethyl, 1-(methylcarbonyloxy)ethyl, 2-(methylcarbonyloxy)-ethyl, 2-(ethylcarbonyloxy)ethyl, 3-(methylcarbonyloxy)-propyl, 4-(methoxycarbonyloxy)butyl, 5-(methoxycarbonyloxy)-pentyl or 6-(methoxycarbonyloxy)hexyl;

($C_1$–$C_6$-alkyl)carbonylthio such as; for example acetylthio, ethylcarbonylthio, n-propylcarbonylthio, 1-methylethylcarbonylthio, n-butylcarbonylthio, 1-methylpropylcarbonylthio, 2-methylpropylcarbonylthio, 1,1-dimethylethylcarbonylthio, n-pentylcarbonylthio, 1-methylbutylcarbonylthio, 2-methylbutylcarbonylthio, 3-methylbutylcarbonylthio, 1,1-dimethylpropylcarbonylthio, 1,2-dimethylpropylcarbonylthio, 2,2-dimethylpropylcarbonylthio, 1-ethylpropylcarbonylthio, n-hexylcarbonylthio, 1-methylpentylcarbonylthio, 2-methylpentylcarbonylthio, 3-methylpentylcarbonylthio, 4-methylpentylcarbonylthio, 1,1-dimethylbutylcarbonylthio, 1,2-dimethylbutylcarbonylthio, 1,3-dimethylbutylcarbonylthio, 2,2-dimethylbutylcarbonylthio, 2,3-dimethylbutylcarbonylthio, 3,3-dimethylbutylcarbonylthio, 1-ethylbutylcarbonylthio, 2-ethylbutylcarbonylthio, 1,1,2-trimethylpropylcarbonylthio, 1,2,2-trimethylpropylcarbonylthio, 1-ethyl-1-methylpropylcarbonylthio or 1-ethyl-2-methylpropylcarbonylthio, in particular acetylthio;

($C_1$–$C_6$-haloalkyl)carbonylthio such as: a ($C_1$–$C_6$-alkyl)-carbonylthio radical as mentioned above which is partially or completely substituted by fluorine, chlorine, bromine and/or iodine, i.e., for example, chloroacetylthio, dichloroacetylthio, trichloroacetylthio, fluoroacetylthio, difluoroacetylthio, trifluoroacetylthio, chlorofluoroacetylthio, dichlorofluoroacetylthio, chlorodifluoroacetylthio, 2-fluoroethylcarbonylthio, 2-chloroethylcarbonylthio, 2-bromoethylcarbonylthio, 2-iodoethylcarbonylthio, 2,2-difluoroethylcarbonylthio, 2,2,2-trifluoroethylcarbonylthio, 2-chloro-2-fluoroethylcarbonylthio, 2-chloro-2,2-difluoroethylcarbonylthio, 2,2-dichloro-2-fluoroethylcarbonylthio, 2,2,2-trichloroethylcarbonylthio, pentafluoroethylcarbonylthio, 2-fluoropropylcarbonylthio, 3-fluoropropylcarbonylthio, 2,2-difluoropropylcarbonylthio, 2,3-difluoropropylcarbonylthio, 2-chloropropylcarbonylthio, 3-chloropropylcarbonylthio, 2,3-dichloropropylcarbonylthio, 2-bromopropylcarbonylthio, 3-bromopropylcarbonylthio, 3,3,3-trifluoropropylcarbonylthio, 3,3,3-trichloropropylcarbonylthio, 2,2,3,3,3-pentafluoropropylcarbonylthio, heptafluoropropylcarbonylthio, 1-(fluoromethyl)-2-fluoroethylcarbonylthio, 1-(chloromethyl)-2-chloroethylcarbonylthio, 1-(bromomethyl)-2-bromoethylcarbonylthio, 4-fluorobutylcarbonylthio, 4-chlorobutylcarbonylthio, 4-bromobutylcarbonylthio or nonafluorobutylcarbonylthio, in particular trifluoroacetylthio;

$C_1$–$C_6$-alkoxy such as: $OCH_3$, $OC_2H_5$, n-propoxy, $OCH(CH_3)_2$, n-butoxy, 1-methylpropoxy, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, in particular methoxy, ethoxy or 1-methylethoxy;

$C_1$–$C_6$-haloalkoxy such as: a $C_1$–$C_6$-alkoxy radical as mentioned above which is partially or completely substituted by fluorine, chlorine, bromine and/or iodine, i.e., for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy;

phenyl-$C_1$–$C_6$-alkoxy such as: for example benzyloxy, 1-phenylethoxy, 2-phenylethoxy, 1-phenylprop-1-yloxy, 2-phenylprop-1-yloxy, 3-phenylprop-1-yloxy, 1-phenylbut-1-yloxy, 2-phenylbut-1-yloxy, 3-phenylbut-1-yloxy, 4-phenylbut-1-yloxy, 1-phenylbut-2-yloxy, 2-phenylbut-2-yloxy, 3-phenylbut-2-yloxy, 3-phenylbut-2-yloxy, 4-phenylbut-2-yloxy, 1-(phenylmethyl)-eth-1-yloxy, 1-(phenylmethyl)-1-(methyl)-eth-1-yloxy or 1-(phenylmethyl)-prop-1-yloxy, in particular benzyloxy or 2-phenylethoxy;

phenyl-$C_1$–$C_6$-alkylthio such as: for example benzylthio, 1-phenylethylthio, 2-phenylethylthio, 1-phenylprop-1-ylthio, 2-phenylprop-1-ylthio, 3-phenylprop-1-ylthio, 1-phenylbut-1-ylthio, 2-phenylbut-1-ylthio, 3-phenylbut-1-ylthio, 4-phenylbut-1-ylthio, 1-phenylbut-2-ylthio, 2-phenylbut-2-ylthio, 3-phenylbut-2-ylthio, 3-phenylbut-2-ylthio, 4-phenylbut-2-ylthio, 1-(phenylmethyl)-eth-1-ylthio, 1-(phenylmethyl)-1-(methyl)-eth-1-ylthio or 1-(phenylmethyl)-prop-1-ylthio, in particular benzylthio or 2-phenylethylthio;

($C_1$–$C_6$-alkoxy)carbonyl such as: CO—OCH$_3$, CO—OC$_2$H$_5$, n-propoxycarbonyl, CO—OCH(CH$_3$)$_2$, n-butoxycarbonyl, 1-methylpropoxycarbonyl, CO—OCH$_2$—CH(CH$_3$)$_2$ or CO—OC(CH$_3$)$_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl, ethoxycarbonyl, CO—OCH(CH$_3$)$_2$, CO—CH$_2$—CH(CH$_3$)$_2$ or 1-methylethoxycarbonyl;

($C_1$–$C_6$-alkoxy)carbonyloxy such as: methoxycarbonyloxy, ethoxycarbonyloxy, n-propoxycarbonyloxy, 1-methylethoxycarbonyloxy, n-butoxycarbonyloxy, 1-methylpropoxycarbonyloxy, 2-methylpropoxycarbonyloxy, 1,1-dimethylethoxycarbonyloxy, n-pentoxycarbonyloxy, 1-methylbutoxycarbonyloxy, 2-methylbutoxycarbonyloxy, 3-methylbutoxycarbonyloxy, 2,2-dimethylpropoxycarbonyloxy, 1-ethylpropoxycarbonyloxy, n-hexoxycarbonyloxy, 1,1-dimethylpropoxycarbonyloxy, 1,2-dimethylpropoxycarbonyloxy, 1-methylpentoxycarbonyloxy, 2-methylpentoxycarbonyloxy, 3-methylpentoxycarbonyloxy, 4-methylpentoxycarbonyloxy, 1,1-dimethylbutoxycarbonyloxy, 1,2-dimethylbutoxycarbonyloxy, 1,3-dimethylbutoxycarbonyloxy, 2,2-dimethylbutoxycarbonyloxy, 2,3-dimethylbutoxycarbonyloxy, 3,3-dimethylbutoxycarbonyloxy, 1-ethylbutoxycarbonyloxy, 2-ethylbutoxycarbonyloxy, 1,1,2-trimethylpropoxycarbonyloxy, 1,2,2-trimethylpropoxycarbonyloxy, 1-ethyl-1-methylpropoxycarbonyloxy or 1-ethyl-2-methylpropoxycarbonyloxy, in particular methoxycarbonyloxy, ethoxycarbonyloxy or 1-methylethoxycarbonyloxy;

($C_1$–$C_6$-alkoxy)carbonylthio such as: methoxycarbonylthio, ethoxycarbonylthio, n-propoxycarbonylthio, 1-methylethoxycarbonylthio, n-butoxycarbonylthio, 1-methylpropoxycarbonylthio, 2-methylpropoxycarbonylthio, 1,1-dimethylethoxycarbonylthio, n-pentoxycarbonylthio, 1-methylbutoxycarbonylthio, 2-methylbutoxycarbonylthio, 3-methylbutoxycarbonylthio, 2,2-dimethylpropoxycarbonylthio, 1-ethylpropoxycarbonylthio, n-hexoxycarbonylthio, 1,1-dimethylpropoxycarbonylthio, 1,2-dimethylpropoxycarbonylthio, 1-methylpentoxycarbonylthio, 2-methylpentoxycarbonylthio, 3-methylpentoxycarbonylthio, 4-methylpentoxycarbonylthio, 1,1-dimethylbutoxycarbonylthio, 1,2-dimethylbutoxycarbonylthio, 1,3-dimethylbutoxycarbonylthio, 2,2-dimethylbutoxycarbonylthio, 2,3-dimethylbutoxycarbonylthio, 3,3-dimethylbutoxycarbonylthio, 1-ethylbutoxycarbonylthio, 2-ethylbutoxycarbonylthio, 1,1,2-trimethylpropoxycarbonylthio, 1,2,2-trimethylpropoxycarbonylthio, 1-ethyl-1-methylpropoxycarbonylthio or 1-ethyl-2-methylpropoxycarbonylthio, in particular methoxycarbonylthio, ethoxycarbonylthio or 1-methylethoxycarbonylthio;

$C_1$–$C_6$-alkylthio such as: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, in particular methylthio or ethylthio;

$C_1$–$C_4$-Haloalkylthio such as: $C_1$–$C_4$-alkylthio such as methylthio, ethylthio, n-propylthio, 1-methylethylthio, n-butylthio, 1-methylpropylthio, 2-methylpropylthio and 1,1-dimethylethylthio, preferably methylthio or ethylthio, which is partially or completely substituted by fluorine, chlorine and/or bromine, i.e., for example, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio, 5-fluoropentylthio, 5-chloropentylthio, 5-bromopentylthio, 5-iodopentylthio, undecafluoropentylthio, 6-fluorohexylthio or 6-chlorohexylthio, in particular trifluoromethylthio, difluoromethylthio, chloromethylthio, fluoromethylthio, 2-fluoroethylthio, 2-chloroethylthio or 2,2,2-trifluoroethylthio;

$C_1$–$C_6$-alkylsulfonyl such as: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular methylsulfonyl;

$C_1$–$C_6$-alkylsulfonyloxy such as: methylsulfonyloxy, ethylsulfonyloxy, n-propylsulfonyloxy, 1-methylethylsulfonyloxy, n-butylsulfonyloxy, 1-methylpropylsulfonyloxy, 2-methylpropylsulfonyloxy, 1,1-dimethylethylsulfonyloxy, n-pentylsulfonyloxy, 1-methylbutylsulfonyloxy, 2-methylbutylsulfonyloxy, 3-methylbutylsulfonyloxy, 1,1-dimethylpropylsulfonyloxy, 1,2-dimethylpropylsulfonyloxy, 2,2-dimethylpropylsulfonyloxy, 1-ethylpropylsulfonyloxy, n-hexylsulfonyloxy, 1-methylpentylsulfonyloxy, 2-methylpentylsulfonyloxy, 3-methylpentylsulfonyloxy, 4-methylpentylsulfonyloxy, 1,1-dimethylbutylsulfonyloxy, 1,2-dimethylbutylsulfonyloxy, 1,3-dimethylbutylsulfonyloxy, 2,2-dimethylbutylsulfonyloxy, 2,3-dimethylbutylsulfonyloxy, 3,3-dimethylbutylsulfonyloxy, 1-ethylbutylsulfonyloxy, 2-ethylbutylsulfonyloxy, 1,1,2-trimethylpropylsulfonyloxy, 1,2,2-trimethylpropylsulfonyloxy, 1-ethyl-1-methylpropylsulfonyloxy or 1-ethyl-2-methylpropylsulfonyloxy, in particular methylsulfonyloxy;

$C_1$–$C_6$-haloalkylsulfonyloxy such as: $C_1$–$C_6$-alkylsulfonyloxy asmentioned above which is partially or completely substituted by fluorine, chlorine, bromine and/or iodine, i.e., for example, $ClCH_2$—$SO_2$—O—, $CH(Cl)_2$—$SO_2$—O—, $C(Cl)_3$—$SO_2$—O—, $FCH_2$—$SO_2$—O—, $CHF_2$—$SO_2$—O—, $CF_3$—$SO_2$—O—, chlorofluoromethyl-$SO_2$—O—, dichlorofluoromethyl-$SO_2$—O—, chlorodifluoromethyl-$SO_2$—O—, 1-fluoroethyl-$SO_2$—O—, 2-fluoroethyl-$SO_2$—O—, 2-chloroethyl-$SO_2$—O—, 2-bromoethyl-$SO_2$—O—, 2-iodoethyl-$SO_2$—O—, 2,2-difluoroethyl-$SO_2$—O—, 2,2,2-trifluoroethyl-$SO_2$—O—, 2-chloro-2-fluoroethyl-$SO_2$—O—, 2-chloro-2,2-difluoroethyl-$SO_2$—O—, 2,2-dichloro-2-fluoroethyl-$SO_2$—O—, 2,2,2-trichloroethyl-$SO_2$—O—, $C_2F_5$—$SO_2$—O—, 2-fluoropropyl-$SO_2$—O—, 3-fluoropropyl-$SO_2$—O—, 2,2-difluoropropyl-$SO_2$—O—, 2,3-difluoropropyl-$SO_2$—O—, 2-chloropropyl-$SO_2$—O—, 3-chloropropyl-$SO_2$—O—, 2,3-dichloropropyl-$SO_2$—O—, 2-bromopropyl-$SO_2$—O—, 3-bromopropyl-$SO_2$—O—, 3,3,3-trifluoropropyl-$SO_2$—O—, 3,3,3-trichloropropyl-$SO_2$—O—, 2,2,3,3,3-pentafluoropropyl-$SO_2$—O—, $C_2F_5$—$CF_2$—$SO_2$—O—, 1-(fluoromethyl)-2-fluoroethyl-$SO_2$—O—, 1-(chloromethyl)-2-chloroethyl-$SO_2$—O—, 1-(bromomethyl)-2-bromoethyl-$SO_2$—O—, 4-fluorobutyl-$SO_2$—O—, 4-chlorobutyl-$SO_2$—O—, 4-bromobutyl-$SO_2$—O—, $C_2F_5$—$CF_2$—$CF_2$—$SO_2$—O—, 5-fluoropentyl-$SO_2$—O—, 5-chloropentyl-$SO_2$—O—, 5-bromopentyl-$SO_2$—O—, 5-iodopentyl-$SO_2$—O—, 5,5,5-trichloropentyl-$SO_2$—O—, $C_2F_5$—$CF_2$—$CF_2$—$CF_2$—$SO_2$—O—, 6-fluorohexyl-$SO_2$—O—, 6-chlorohexyl-$SO_2$—O—, 6-bromohexyl-$SO_2$—O—, 6-iodohexyl-$SO_2$—O—, 6,6,6-trichlorohexyl-$SO_2$—O— or dodecafluorohexyl-$SO_2$—O—, in particular $CF_3$—$SO_2$—O—;

$C_1$–$C_4$-alkylamino such as: methylamino, ethylamino, n-propylamino, 1-methylethylamino, n-butylamino, 1-methylpropylamino, 2-methylpropylamino or 1,1-dimethylethylamino, in particular methylamino or ethylamino;

($C_1$–$C_4$-alkylamino)carbonyl such as: CO—NH—$CH_3$, CO—NH—$C_2H_5$, n-propylaminocarbonyl, CO—NH—$CH(CH_3)_2$, n-butylaminocarbonyl, 1-methylpropylaminocarbonyl, CO—NH—$CH_2$—CH($CH_3$)$_2$ or CO—NH—$C(CH_3)_3$, in particular CO—NH—$CH_3$ or CO—NH—$C_2H_5$;

($C_1$–$C_6$-alkylamino)carbonyl such as: ($C_1$–$C_4$-alkylamino)carbonyl as mentioned above plus, for example, n-pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, n-hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-meethylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2- trimethylpropylaminocarbonyl, 1-ethyl-1-methylpropylaminocarbonyl or 1-ethyl-2-methylpropylaminocarbonyl, in particular CO—NH—CH$_3$, CO—NH—C$_2$H$_5$ or CO—NH—CH(CH$_3$)$_2$;

di(C$_1$–C$_6$-alkyl)aminocarbonyl such as: for example N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)-aminocarbonyl, N-butyl-N-methylaminocarbonyl, N-methyl-N-(1-methylpropyl)aminocarbonyl, N-methyl-N-(2-methylpropyl)-aminocarbonyl, N-(1,1-dimethylethyl)-N-methylaminocarbonyl, N-ethyl-N-propylaminocarbonyl, N-ethyl-N-(1-methylethyl)-aminocarbonyl, N-butyl-N-ethylaminocarbonyl, N-ethyl-N-(1-methylpropyl)aminocarbonyl, N-ethyl-N-(2-methylpropyl)-aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminccarbonyl, N-(1,1-dimethylethyl)-N-(1-methylpropyl)aminocarbonyl or N-(1,1-dimethylethyl)-N-(2-methylpropyl)aminocarbonyl, in particular N,N-dimethylaminocarbonyl or N,N-diethylaminocarbonyl;

C$_1$–C$_6$-alkoxy-C$_1$–C$_6$-alkyl such as: C$_1$–C$_6$-alkyl substituted by C$_1$–C$_6$-alkoxy as mentioned above, i.e., for example, methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)-propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular methoxymethyl or 2-methoxyethyl;

C$_1$–C$_6$-alkoxy-C$_1$–C$_6$-alkoxy such as: C$_1$–C$_6$-alkoxy substituted by C$_1$–C$_6$-alkoxy as mentioned above, i.e., for example, methoxymethoxy, ethoxymethoxy, n-propoxymethoxy, (1-methylethoxy)methoxy, n-butoxymethoxy, (1-methylpropoxy)methoxy, (2-methylpropoxy)methoxy, (1,1-dimethylethoxy)methoxy, 2-(methoxy)ethoxy, 2-(ethoxy)ethoxyi 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxyg 2-(n-butoxy)propoxy, 2-(1-methylpropoxy)propoxy, 2-(2-methylpropoxy)propoxy, 2-(1,1-dimethylethoxy)propoxy, 3-(methoxy)-propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)-butoxy, 2-(1-methylpropoxy)butoxy, 2-(2-methylpropoxy)butoxy, 2-(1,1-dimethylethoxy)butoxy, 3-(methoxy)butoxy, 3-(ethoxy)-butoxy, 3-(n-propoxy)butoxy, 3-(1-methylethoxy)butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-methylethoxy)butoxy, 4-(n-butoxy)butoxy, 4-(1-methylpropoxy)butoxy, 4-(2-methylpropoxy)butoxy, 4-(1,1-dimethylethoxy)butoxy, 5-(methoxy)pentoxy, 5-(ethoxy)pentoxy, 5-(n-propoxy)pentoxy, 5-(1-methylethoxy)pentoxy, 5-(n-butoxy)pentoxy, 5-(1-methylpropoxy)pentoxy, 5-(2-methylpropoxy)pentoxy, 5-(1,1-dimethylethoxy)pentoxy, 6-(methoxy)hexoxy, 6-(ethoxy)hexoxy, 6-(n-propoxy)hexoxy, 6-(1-methylethoxy)hexoxy, 6-(n-butoxy)-hexoxy, 6-(1-methylpropoxy)hexoxy, 6-(2-methylpropoxy)hexoxy or 6-(1,1-dimethylethoxy)hexoxy, in particular methoxymethoxy or ethoxymethoxy;

(C$_1$–C$_6$-alkoxy)carbonyl-C$_1$–C6-alkoxy such as: C$_1$–C$_6$-alkoxy substituted by (C$_1$–C$_6$-alkoxy)carbonyl as mentioned above, i.e., for example, OCH$_2$—CO—OCH$_3$, OCH$_2$—CO—OC$_2$H$_5$, OCH$_2$—CO—OCH$_2$—C$_2$H$_5$, OCH$_2$—CO—OCH(CH$_3$)$_2$, n-butoxycarbonylmethoxy, 1-(methoxycarbonyl)ethoxy, 2-(methoxycarbonyl)ethoxy, 2-(ethoxycarbonyl)ethoxy, 2-(n-propoxycarbonyl)ethoxy, 2-(n-butoxycarbonyl)ethoxy, 3-(methoxycarbonyl)propoxy, 3-(ethoxycarbonyl)propoxy, 3-(n-propoxycarbonyl)propoxy, 3-(n-butoxycarbonyl)propoxy, 4-(methoxycarbonyl)butoxy, 4-(ethoxycarbonyl)butoxy, 4-(n-propoxycarbonyl)butoxy, 4-(n-butoxycarbonyl)butoxy, 5-(methoxycarbonyl)pentoxy, 5-(ethoxycarbonyl)pentoxy, 5-(n-propoxycarbonyl)pentoxy, 5-(n-butoxycarbonyl)butoxy, 6-(methoxycarbonyl)hexoxy, 6-(ethoxycarbonyl)hexoxy, 6-(n-propoxycarbonyl)hexoxy or 6-(n-butoxycarbonyl)hexoxy, in particular OCH$_2$—CO—OCH$_3$ or 1-(methoxycarbonyl)ethoxy;

C$_1$–C$_6$-alkoxy)carbonyl-C$_1$–C$_6$-alkyl such as: C$_1$–C$_6$-alkyl substituted by (C$_1$–C$_6$-alkoxy)carbonyl as mentioned above, i.e., for example, methoxycarbonylmethyl, ethoxycarbonylmethyl, 1-(methoxycarbonyl)ethyl, 2-(methoxycarbonyl)ethyl, 2-(ethoxycarbonyl)ethyl, 3-(methoxycarbonyl)propyl, 4-(methoxycarbonyl)butyl, 5-(methoxycarbonyl)pentyl or 6-(methoxycarbonyl)hexyl;

($C_1$–$C_6$-alkoxy)carbonyl-$C_1$–$C_6$-alkylsulfonyl such as: $C_1$–$C_6$-alkylsulfonyl substituted by ($C_1$–$C_6$-alkoxy) carbonyl as mentioned above, i.e., for example, methoxycarbonylmethylsulfonyl, ethoxycarbonylmethylsulfonyl, 1-(methoxycarbonyl)ethylsulfonyl, 2-(methoxycarbonyl)ethylsulfonyl, 2-(ethoxycarbonyl)ethylsulfonyl, 3-(methoxycarbonyl)propylsulfonyl, 4-(methoxycarbonyl)butylsulfonyl, 5-(methoxycarbonyl)pentylsulfonyl or 6-(methoxycarbonyl)hexylsulfonyl;

$C_1$–C6-alkylthio-$C_1$–$C_6$-alkyl such as: $C_1$–$C_6$-alkyl substituted by $C_1$–$C_6$-alkylthio as mentioned above, i.e., for example, $CH_2$—$SCH_3$, $CH_2$—$SC_2H_5$, n-propylthiomethyl, $CH_2$—$SCH(CH_3)_2$, n-butylthiomethyl, (1-methylpropylthio)methyl, $CH_2$—$SCH_2$—$CH(CH_3)_2$, $CH_2$—$SC(CH_3)_3$, 2-methylthioethyl, 2-ethylthioethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 3-(methylthio)propyl, 2-(ethylthio)propyl, 3-(ethylthio)propyl, 3-(propylthio)propyl, 3-(butylthio)propyl, 4-(methylthio)butyl, 4-(ethylthio)butyl, 4-(n-propylthio)butyl or 4-(n-butylthio)butyl, in particular 2-(methylthio)ethyl;

$C_1$–C6-alkylthio-($C_1$–C6-alkyl)carbonyl such as: ($C_1$–$C_6$-alkyl)carbonyl substituted by $C_1$–$C_6$-alkylthio as mentioned above, preferably $SCH_3$ or $SC_2H_5$, i.e., for example, methylthiomethylcarbonyl, ethylthiomethylcarbonyl, 1-(methylthio)ethylcarbonyl, 2-(methylthio)ethylcarbonyl, 3-(methylthio)propylcarbonyl, 4-(methylthio)butylcarbonyl, 5(methylthio)pentylcarbonyl or 6-(methylthio)hexylcarbonyl, in particular CO—$CH_2$—$SCH_3$ or CO—$CH(CH_3)$—$SCH_3$;

di($C_1$–$C_6$-alkyl)amino-$C_1$–$C_6$-alkoxy such as: $C_1$–$C_6$-alkoxy which is substituted by di($C_1$–$C_6$-alkyl)amino such as $N(CH_3)_2$, $N(C_2H_5)_2$, N,N-dipropylamino, N,N-di(1-methylethyl)amino, N,N-dibutylamino, N,N-di(1-methylpropyl)amino, N,N-di(2-methylpropyl)amino, $N[C(CH_3)_3]_2$, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)-amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably N,N-dimethylamino or N,N-diethylamino, i.e., for example, $OCH_2$—$N(CH_3)_2$, $OCH_2$—$N(C_2H_5)_2$, $OCH(CH_3)$—$N(CH_3)_2$, 2-(dimethylamino)ethoxy, $OCH(CH_3)$—$N(C_2H_5)_2$, 3-(dimethylamino)propoxy, 4-(dimethylamino)butoxy, 5-(dimethylamino)pentoxy or 6-(dimethylamino)hexoxy, in particular $OCH_2$—$N(CH_3)_2$ or $OCH(CH_3)$—$N(CH_3)_2$;

$C_3$–$C_6$-alkenyl such as: for example prop-2-en-1-yl, n-buten-4-yl, 1-methylprop-2-en-1-yl, 2-methyl-prop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular prop-2-en-1-yl or n-buten-4-yl;

$C_2$–$C_6$-alkenyl such as: ethenyl or one of the radicals mentioned for $C_3$–$C_6$-alkenyl, in particular ethenyl or prop-2-en-1-yl;

$C_3$–$C_6$-haloalkenyl such as: $C_3$–$C_6$-alkenyl as mentioned above which is partially or completely substituted by fluorine, chlorine and/or bromine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

phenyl-$C_3$–$C_6$-alkenyloxy such as: for example 3-phenylallyloxy, 4-phenylbut-2-enyloxy, 4-phenyl-but-3-enyloxy or 5-phenylpent-4-enyloxy, preferably 3-phenylallyloxy or 4-phenylbut-2-enyloxy, in particular 3-phenylallyloxy;

Heterocyclyl-$C_3$–$C_6$-alkenyloxy such as: for example, 3-heterocyclylallyloxy, 4-heterocyclylbut-2-enyloxy, 4-heterocyclylbut-3-enyloxy or 5-heterocyclylpent-4-enyloxy, preferably 3-heterocyclylallyloxy or 4-heterocyclylbut-2-enyloxy, in particular 3-heterocyclylallyloxy;

$C_3$–$C_6$-alkenyloxy such as: prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-Penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1- yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, in particular prop-2-en-1-yloxy;

$C_2$–$C_6$-alkenyloxy such as: ethenyloxy or one of the radicals mentioned for $C_3$–$C_6$-alkenyloxy, in particular ethenyloxy or prop-2-en-1-yloxy;

$C_3$–$C_6$-haloalkenyloxy such as: $C_3$–$C_6$-alkenyloxy as mentioned above which is partially or completely substituted by fluorine, chlorine and/or bromine; i.e., for example, 2-chloroallyloxy, 3-chloroallyloxy, 2,3-dichloroallyloxy, 3,3-dichloroallyloxy, 2,3,3-trichloroallyloxy, 2,3-dichlorobut-2-enyloxy, 2-bromoallyloxy, 3-bromoallyloxy, 2,3-dibromoallyloxy, 3,3-dibromoallyloxy, 2,3,3-tribromoallyloxy or 2,3-dibromobut-2-enyloxy, in particular 2-chloroallyloxy or 3,3-dichloroallyloxy;

$C_3$–$C_6$-alkenylthio such as: prop-1-en-1-ylthio, prop-2-en-1-ylthio, 1-methylethenylthio, n-buten-1-ylthio, n-buten-2-ylthio, n-buten-3-ylthio, 1-methylprop-1-en-1-ylthio, 2-methylprop-1-en-1-ylthio, 1-methylprop-2-en-1-ylthio, 2-methylprop-2-en-1-ylthio, n-penten-1-ylthio, n-penten-2-ylthio, n-penten-3-ylthio, n-penten-4-ylthio, 1-methylbut-1-en-1-ylthio, 2-methylbut-1-en-1-ylthio, 3-methylbut-1-en-1-ylthio, 1-methylbut-2-en-1-ylthio, 2-methylbut-2-en-1-ylthio, 3-methylbut-2-en-1-ylthio, 1-methylbut-3-en-1-ylthio, 2-methylbut-3-en-1-ylthio, 3-methylbut-3-en-1-ylthio, 1,1-dimethylprop-2-en-1-ylthio, 1,2-dimethylprop-1-en-1-ylthio, 1,2-dimethylprop-2-en-1-ylthio, 1-ethylprop-1-en-2-ylthio, 1-ethylprop-2-en-1-ylthio, n-hex-1-en-1-ylthio, n-hex-2-en-1-ylthio, n-hex-3-en-1-ylthio, n-hex-4-en-1-ylthio, n-hex-5-en-1-ylthio, 1-methylpent-1-en-1-ylthio, 2-methylpent-1-en-1-ylthio, 3-methylpent-1-en-1-ylthio, 4-methylpent-1-en-1-ylthio, 1-methylpent-2-en-1-ylthio, 2-methylpent-2-en-1-ylthio, 3-methylpent-2-en-1-ylthio, 4-methylpent-2-en-1-ylthio, 1-methylpent-3-en-1-ylthio, 2-methylpent-3-en-1-ylthio, 3-methylpent-3-en-1-ylthio, 4-methylpent-3-en-1-ylthio, 1-methylpent-4-en-1-ylthio, 2-methylpent-4-en-1-ylthio, 3-methylpent-4-en-1-ylthio, 4-methylpent-4-en-1-ylthio, 1,1-dimethylbut-2-en-1-ylthio, 1,1-dimethylbut-3-en-1-ylthio, 1,2-dimethylbut-1-en-1-ylthio, 1,2-dimethylbut-2-en-1-ylthio, 1,2-dimethylbut-3-en-1-ylthio, 1,3-dimethylbut-1-en-1-ylthio, 1,3-dimethylbut-2-en-1-ylthio, 1,3-dimethylbut-3-en-1-ylthio, 2,2-dimethylbut3-en-1-ylthio, 2,3-dimethylbut-1-en-1-ylthio, 2,3-dimethylbut-2-en-1-ylthio, 2,3-dimethylbut-3-en-1-ylthio, 3,3-dimethylbut-1-en-1-ylthio, 3,3-dimethylbut-2-en-1-ylthio, 1-ethylbut-1-en-1-ylthio, 1-ethylbut-2-en-1-ylthio, 1-ethylbut-3-en-1-ylthio, 2-ethylbut-1-en-1-ylthio, 2-ethylbut-2-en-1-ylthio, 2-ethylbut-3-en-1-ylthio, 1,1,2-trimethylprop-2-en-1-ylthio, 1-ethyl-1-methylprop-2-en-1-ylthio, 1-ethyl-2-methylprop-1-en-1-ylthio or 1-ethyl-2-methylprop-2-en-1-ylthio, in particular prop-2-en-1-ylthio;

$C_2$–$C_6$-alkenylthio such as: ethenylthio or one of the radicals mentioned for $C_3$–$C_6$-alkenylthio, in particular ethenylthio or prop-2-en-1-ylthio;

$C_3$–$C_6$-alkynyl such as: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methyipent-2-yn-4-yl or 4-methylpent-2-yn-5-yl, in particular prop-2-yn-1-yl;

$C_2$–$C_6$-alkynyl such as: ethynyl or one of the radicals mentioned for $C_3$–$C_6$-alkynyl, in particular ethynyl or prop-2-yn-1-yl;

$C_3$–$C_6$-alkynyloxy such as: prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular prop-2-yn-1-yloxy;

$C_2$–$C_6$-alkynyloxy such as: ethynyloxy or one of the radicals mentioned for $C_3$–$C_6$-alkynyloxy, in particular ethynyloxy or prop-2-yn-1-yloxy;

($C_3$–$C_6$-alkenyl)oxycarbonyl such as: prop-1-en-1-yloxycarbonyl, prop-2-en-1-yloxycarbonyl, 1-methylethenyloxycarbonyl, n-buten-1-yloxycarbonyl, n-buten-2-yloxycarbonyl, n-buten-3-yloxycarbonyl, 1-methylprop-1-en-1-yloxycarbonyl, 2-methylprop-1-en-1-yloxycarbonyl, 1-methylprop-2-en-1-yloxycarbonyl, 2-methylprop-2-en-1-yloxycarbonyl, n-penten-1-yloxycarbonyl, n-penten-2-yloxycarbonyl, n-penten-3-yloxycarbonyl, n-penten-4-yloxycarbonyl, 1-methylbut-1-en-1-yloxycarbonyl, 2-methylbut-1-en-1-yloxycarbonyl, 3-methylbut-1-en-1-yloxycarbonyl, 1-methylbut-2-en-1-yloxycarbonyl, 2-methylbut-2-en-1-yloxycarbonyl, 3-methylbut-2-en-1-yloxycarbonyl, 1-methylbut-3-en-1-yloxycarbonyl, 2-methylbut-3-en-1-yloxycarbonyl, 3-methylbut-3-en-1-yloxycarbonyl, 1,1-dimethylprop-2-en-1-yloxycarbonyl, 1,2-dimethylprop-1-en-1-yloxycarbonyl, 1,2-dimethylprop-2-en-1-yloxycarbonyl, 1-ethylprop-1-en-2-yloxycarbonyl, 1-ethylprop-2-en-1-yloxycarbonyl, n-hex-1-en-1-yloxycarbonyl, n-hex-2-en-1-yloxycarbonyl, n-hex-3-en-1-yloxycarbonyl, n-hex-4-en-1-yloxycarbonyl, n-hex-5-en-1-yloxycarbonyl, 1-methylpent-1-en-1-yloxycarbonyl, 2-methylpent-1-en-1-yloxycarbonyl, 3-methylpent-1-en-1-yloxycarbonyl, 4-methylpent-1-en-1-yloxycarbonyl, 1-methylpent-2-en-1-yloxycarbonyl, 2-methylpent-2-en-1-yloxycarbonyl, 3-methylpent-2-en-1-yloxycarbonyl, 4-methylpent-2-en-1-yloxycarbonyl, 1-methylpent-3-en-1-yloxycarbonyl, 2-methylpent-3-en-1-yloxycarbonyl, 3-methylpent-3-en-1-yloxycarbonyl, 4-methylpent-3-en-1-yloxycarbonyl, 1-methylpent-4-en-1-yloxycarbonyl, 2-methylpent-4-en-1-yloxycarbonyl, 3-methylpent-4-en-1-yloxycarbonyl, 4-methylpent-4-en-1-yloxycarbonyl, 1,1-dimethylbut-2-en-1-yloxycarbonyl, 1,1-dimethylbut-3-en-1-yloxycarbonyl, 1,2-dimethylbut-1-en-1-yloxycarbonyl, 1,2-dimethylbut-2-en-1-yloxycarbonyl, 1,2-dimethylbut-3-en-1-yloxycarbonyl, 1,3-dimethylbut-1-en-1-yloxycarbonyl, 1,3-dimethylbut-2-en-1-yloxycarbonyl, 1,3-dimethylbut-3-en-1-yloxycarbonyl, 2,2-dimethylbut-3-en-1-yloxycarbonyl, 2,3-dimethylbut-1-en-1-yloxycarbonyl, 2,3-dimethylbut-2-en-1-yloxycarbonyl, 2,3-dimethylbut-3-en-1-yloxycarbonyl, 3,3-dimethylbut-1-en-1-yloxycarbonyl, 3,3-dimethylbut-2-en-1-yloxycarbonyl, 1-ethylbut-1-en-1-yloxycarbonyl, 1-ethylbut-2-en-1-yloxycarbonyl, 1-ethylbut-3-en-1-yloxycarbonyl, 2-ethylbut-1-en-1-yloxycarbonyl, 2-ethylbut-2-en-1-yloxycarbonyl, 2-ethylbut-3-en-1-yloxycarbonyl, 1,1,2-trimethylprop-2-en-1-yloxycarbonyl, 1-ethyl-1-methylprop-2-en-1-yloxycarbonyl, 1-ethyl-2-methylprop-1-en-1-yloxycarbonyl or 1-ethyl-2-methylprop-2-en-1-yloxycarbonyl, in particular prop-2-en-1-yloxycarbonyl;

($C_3$–$C_6$-alkenyloxy)carbonyl-$C_1$–$C_6$-alkyl such as: $C_1$–$C_6$-alkyl substituted by ($C_3$–$C_6$-alkenyloxy) carbonyl as mentioned above, preferably prop-2-en-1-yloxycarbonyl, i.e., for example, prop-2-en-1-yloxycarbonylmethyl;

($C_3$–$C_6$-alkenyl)carbonyloxy such as: prop-1-en-1-ylcarbonyloxy, prop-2-en-1-ylcarbonyloxy, 1-methylethenylcarbonyloxy, n-buten-1-ylcarbonyloxy, n-buten-2-ylcarbonyloxy, n-buten-3-ylcarbonyloxy, 1-methylprop-1-en-1-ylcarbonyloxy, 2-methylprop-1-en-1-ylcarbonyloxy, 1-methylprop-2-en-1-ylcarbonyloxy, 2-methylprop-2-en-1-ylcarbonyloxy, n-penten-1-ylcarbonyloxy, n-penten-2-ylcarbonyloxy, n-penten-3-ylcarbonyloxy, n-penten-4-ylcarbonyloxy, 1-methylbut-1-en-1-ylcarbonyloxy, 2-methylbut-1-en-1-ylcarbonyloxy, 3-methylbut-1-en-1-ylcarbonyloxy, 1-methylbut-2-en-1-ylcarbonyloxy, 2-methylbut-2-en-1-ylcarbonyloxy, 3-methylbut-2-en-1-ylcarbonyloxy, 1-methylbut-3-en-1-ylcarbonyloxy, 2-methylbut-3-en-1-ylcarbonyloxy, 3-methylbut-3-en-1-ylcarbonyloxy, 1,1-dimethylprop-2-en-1-ylcarbonyloxy, 1,2-dimethylprop-1-en-1-ylcarbonyloxy, 1,2-dimethylprop-2-en-1-ylcarbonyloxy, 1-ethylprop-1-en-2-ylcarbonyloxy, 1-ethylprop-2-en-1-ylcarbonyloxy, n-hex-1-en-1-ylcarbonyloxy, n-hex-2-en-1-ylcarbonyloxy, n-hex-3-en-1-ylcarbonyloxy, n-hex-4-en-1-ylcarbonyloxy, n-hex-5-en-1-ylcarbonyloxy, 1-methylpent-1-en-1-ylcarbonyloxy, 2-methylpent-1-en-1-ylcarbonyloxy, 3-methylpent-1-en-1-ylcarbonyloxy, 4-methylpent-1-en-1-ylcarbonyloxy, 1-methylpent-2-en-1-ylcarbonyloxy, 2-methylpent-2-en-1-ylcarbonyloxy, 3-methylpent-2-en-1-ylcarbonyloxy, 4-methylpent-2-en-1-ylcarbonyloxy, 1-methylpent-3-en-1-ylcarbonyloxy, 2-methylpent-3-en-1-ylcarbonyloxy, 3-methylpent-3-en-1-ylcarbonyloxy, 4-methylpent-3-en-1-ylcarbonyloxy, 1-methylpent-4-en-1-ylcarbonyloxy, 2-methylpent-4-en-1-ylcarbonyloxy, 3-methylpent-4-en-1-ylcarbonyloxy, 4-methylpent-4-en-1-ylcarbonyloxy, 1,1-dimethylbut-2-en-1-ylcarbonyloxy, 1,1-dimethylbut-3-en-1-ylcarbonyloxy, 1,2-dimethylbut-1-en-1-ylcarbonyloxy, 1,2-dimethylbut-2-en-1-ylcarbonyloxy, 1,2-dimethylbut-3-en-1-ylcarbonyloxy, 1,3-dimethylbut-1-en-1-ylcarbonyloxy, 1,3-dimethylbut-2-en-1-ylcarbonyloxy, 1,3-dimethylbut-3-en-1-ylcarbonyloxy, 2,2-dimethylbut-3-en-1-ylcarbonyloxy, 2,3-dimethylbut-1-en-1-ylcarbonyloxy, 2,3-dimethylbut-2-en-1-ylcarbonyloxy, 2,3-dimethylbut-3-en-1-ylcarbonyloxy, 3,3-dimethylbut-1-en-1-ylcarbonyloxy, 3,3-dimethylbut-2-en-1-ylcarbonyloxy, 1-ethylbut-1-en-1-ylcarbonyloxy, 1-ethylbut-2-en-1-ylcarbonyloxy, 1-ethylbut-3-en-1-ylcarbonyloxy, 2-ethylbut-1-en-1-ylcarbonyloxy, 2-ethylbut-2-en-1-ylcarbonyloxy, 2-ethylbut-3-en-1-ylcarbonyloxy, 1,1,2-trimethylprop-2-en-1-ylcarbonyloxy, 1-ethyl-1-methylprop-2-en-1-ylcarbonyloxy, 1-ethyl-2-methylprop-1-en-1-ylcarbonyloxy or 1-ethyl-2-methylprop-2-en-1-ylcarbonyloxy, in particular prop-2-en-1-ylcarbonyloxy;

($C_2$–$C_6$-alkenyl)carbonyloxy such as: ethenylcarbonyloxy or one of the radicals mentioned for ($C_3$–$C_6$-alkenyl)carbonyloxy, in particular ethenylcarbonyloxy or prop-2-en-1-ylcarbonyloxy;

($C_3$–$C_6$-alkenyl)carbonylthio such as: prop-1-en-1-ylcarbonylthio, prop-2-en-1-ylcarbonylthio, 1-methylethenylcarbonylthio, n-buten-1-ylcarbonylthio, n-buten-2-ylcarbonylthio, n-buten-3-ylcarbonylthio, 1-methylprop-1-en-1-ylcarbonylthio, 2-methylprop-1-en-1-ylcarbonylthio, 1-methylprop-2-en-1-ylcarbonylthio, 2-methylprop-2-en-1-ylcarbonylthio, n-penten-1-ylcarbonylthio, n-penten-2-ylcarbonylthio, n-penten-3-ylcarbonylthio, n-penten-4-ylcarbonylthio, 1-methylbut-1-en-1-ylcarbonylthio, 2-methylbut-1-en-1-ylcarbonylthio, 3-methylbut-1-en-1-ylcarbonylthio, 1-methylbut-2-en-1-ylcarbonylthio, 2-methylbut-2-en-1-ylcarbonylthio, 3-methylbut-2-en-1-ylcarbonylthio, 1-methylbut-3-en-1-ylcarbonylthio, 2-methylbut-3-en-1-ylcarbonylthio, 3-methylbut-3-en-1-ylcarbonylthio, 1,1-dimethylprop-2-en-1-ylcarbonylthio, 1,2-dimethylprop-1-en-1-ylcarbonylthio, 1,2-dimethylprop-2-en-1-ylcarbonylthio, 1-ethylprop-1-en-2-ylcarbonylthio, 1-ethylprop-2-en-1-ylcarbonylthio, n-hex-1-en-1-ylcarbonylthio, n-hex-2-en-1-ylcarbonylthio, n-hex-3-en-1-ylcarbonylthio, n-hex-4-en-1-ylcarbonylthio, n-hex-5-en-1-ylcarbonylthio, 1-methylpent-1-en-1-ylcarbonylthio, 2-methylpent-1-en-1-ylcarbonylthio, 3-methylpent-1-en-1-ylcarbonylthio, 4-methylpent-1-en-1-ylcarbonylthio, 1-methylpent-2-en-1-ylcarbonylthio, 2-methylpent-2-en-1-ylcarbonylthio, 3-methylpent-2-en-1-ylcarbonylthio, 4-methylpent-2-en-1-ylcarbonylthio, 1-methylpent-3-en-1-ylcarbonylthio, 2-methylpent-3-en-1-ylcarbonylthio, 3-methylpent-3-en-1-ylcarbonylthio, 4-methylpent-3-en-1-ylcarbonylthio, 1-methylpent-4-en-1-ylcarbonylthio, 2-methylpent-4-en-1-ylcarbonylthio, 3-methylpent-4-en-1-ylcarbonylthio, 4-methylpent-4- en-1-ylcarbonylthio, 1,1-dimethylbut-2-en-1-ylcarbonylthio, 1,1-dimethylbut-3-en-1-ylcarbonylthio, 1,2-dimethylbut-1-en-1-ylcarbonylthio, 1,2-dimethylbut-2-en-1-ylcarbonylthio, 1,2-dimethylbut-3-en-1-ylcarbonylthio, 1,3-dimethylbut-1-en-1-ylcarbonylthio, 1,3-dimethylbut-2-en-1-ylcarbonylthio, 1,3-dimethylbut-3-en-1-ylcarbonylthio, 2,2-dimethylbut-3-en-1-ylcarbonylthio, 2,3-dimethylbut-1-en-1-ylcarbonylthio, 2,3-dimethylbut-2-en-1-ylcarbonylthio, 2,3-dimethylbut-3-en-1-ylcarbonylthio, 3,3-dimethylbut-1-en-1-ylcarbonylthio, 3,3-dimethylbut-2-en-1-ylcarbonylthio, 1-ethylbut-1-en-1-ylcarbonylthio, 1-ethylbut-2-en-1-ylcarbonylthio, 1-ethylbut-3-en-1-ylcarbonylthio, 2-ethylbut-1-en-1-ylcarbonylthio, 2-ethylbut-2-en-1-ylcarbonylthio, 2-ethylbut-3-en-1-ylcarbonylthio, 1,1,2-trimethylprop-2-en-1-ylcarbonylthio, 1-ethyl-1-methylprop-2-en-1-ylcarbonylthio, 1-ethyl-2-methylprop-1-en-1-ylcarbonylthio or 1-ethyl-2-methylprop-2-en-1-ylcarbonylthio, in particular prop-2-en-1-ylcarbonylthio;

($C_2$–$C_6$-alkenyl)carhonylthio such as: ethenylcarbonylthio or one of the radicals mentioned for ($C_3$–$C_6$-alkenyl)carbonylthio, in particular prop-2-en-1-ylcarbonylthio;

($C_3$–$C_6$-alkynyl)carbonyloxy such as: prop-1-yn-1-ylcarbonyloxy, prop-2-yn-1-ylcarbonyloxy, n-but-1-yn-1-ylcarbonyloxy, n-but-1-yn-3-ylcarbonyloxy, n-but-1-yn-4-ylcarbonyloxy, n-but-2-yn-1-ylcarbonyloxy, n-pent-1-yn-1-ylcarbonyloxy, n-pent-1-yn-3-ylcarbonyloxy, n-pent-1-yn-4-ylcarbonyloxy, n-pent-1-yn-5-ylcarbonyloxy, n-pent-2-yn-1-ylcarbonyloxy, n-pent-2-yn-4-ylcarbonyloxy, n-pent-2-yn-5-ylcarbonyloxy, 3-methylbut-1-yn-3-ylcarbonyloxy, 3-methylbut-1-yn-4-ylcarbonyloxy, n-hex-1-yn-1-ylcarbonyloxy, n-hex-1-yn-3-ylcarbonyloxy, n-hex-1-yn-4-ylcarbonyloxy, n-hex-1-yn-5-ylcarbonyloxy, n-hex-1-yn-6-ylcarbonyloxy, n-hex-2-yn-1-ylcarbonyloxy, n-hex-2-yn-4-ylcarbonyloxy, n-hex-2-yn-5-ylcarbonyloxy, n-hex-2-yn-6-ylcarbonyloxy, n-hex-3-yn-1-ylcarbonyloxy, n-hex-3-yn-2-ylcarbonyloxy, 3-methylpent-1-yn-1-ylcarbonyloxy, 3-methylpent-1-yn-3-ylcarbonyloxy, 3-methylpent-1-yn-4-ylcarbonyloxy, 3-methylpent-1-yn-5-ylcarbonyloxy, 4-methylpent-1-yn-1-ylcarbonyloxy, 4-methylpent-2-yn-4-ylcarbonyloxy or 4-methylpent-2-yn-5-ylcarbonyloxy, in particular prop-2-yn-1-ylcarbonyloxy;

($C_2$–$C_6$-alkynyl)carbonyloxy such as: ethynylcarbonyloxy or one of the radicals mentioned for ($C_3$–$C_6$-alkynyl)carbonyloxy, in particular ethynylcarbonyloxy or prop-2-yn-1-ylcarbonyloxy;

$C_3$–$C_6$-alkynylsulfonyloxy such as: prop-1-yn-1-ylsulfonyloxy, prop-2-yn-1-ylsulfonyloxy, n-but-1-yn-1-ylsulfonyloxy, n-but-1-yn-3-ylsulfonyloxy, n-but-1-yn-4-ylsulfonyloxy, n-but-2-yn-1-ylsulfonyloxy, n-pent-1-yn-1-ylsulfonyloxy, n-pent-1-yn-3-ylsulfonyloxy, n-pent-1-yn-4-ylsulfonyloxy, n-pent-1-yn-5-ylsulfonyloxy, n-pent-2-yn-1-ylsulfonyloxy, n-pent-2-yn-4-ylsulfonyloxy, n-pent-2-yn-5-ylsulfonyloxy, 3-methylbut-1-yn-3-ylsulfonyloxy, 3-methylbut-1-yn-4-ylsulfonyloxy, n-hex-1-yn-1-ylsulfonyloxy, n-hex-1-yn-3-ylsulfonyloxy, n-hex-1-yn-4-ylsulfonyloxy, n-hex-1-yn-5-ylsulfonyloxy, n-hex-1-yn-6-ylsulfonyloxy, n-hex-2-yn-1-ylsulfonyloxy, n-hex-2-yn-4-ylsulfonyloxy, n-hex-2-yn-5-ylsulfonyloxy, n-hex-2-yn-6-ylsulfonyloxy, n-hex-3-yn-1-ylsulfonyloxy, n-hex-3-yn-2-ylsulfonyloxy, 3-methylpent-1-yn-1-ylsulfonyloxy, 3-methylpent-1-yn-3-ylsulfonyloxy, 3-methylpent-1-yn-4-ylsulfonyloxy, 3-methylpent-1-yn-5-ylsulfonyloxy, 4-methylpent-1-yn-1-ylsulfonyloxy, 4-methylpent-2-yn-4-ylsulfonyloxy or 4-methylpent-2-yn-5-ylsulfonyloxy, in particular prop-2-yn-1-ylsulfonyloxy;

($C_3$–$C_6$-alkynyl)carbonylthio such as: prop-1-yn-1-ylcarbonylthio, prop-2-yn-1-ylcarbonylthio, n-but-1-yn-1-ylcarbonylthio, n-but-1-yn-3-ylcarbonylthio, n-but-1-yn-4-ylcarbonylthio, n-but-2-yn-1-ylcarbonylthio, n-pent-1-yn-1-ylcarbonylthio, n-pent-1-yn-3-ylcarbonylthio, n-pent-1-yn-4-ylcarbonylthio, n-pent-1-yn-5-ylcarbonylthio, n-pent-2-yn-1-ylcarbonylthio, n-pent-2-yn-4-ylcarbonylthio, n-pent-2-yn-5-ylcarbonylthio, 3-methylbut-1-yn-3-ylcarbonylthio, 3-methylbut-1-yn-4-ylcarbonylthio, n-hex-1-yn-1-ylcarbonylthio, n-hex-1-yn-3-ylcarbonylthio, n-hex-1-yn-4-ylcarbonylthio, n-hex-1-yn-5-ylcarbonylthio, n-hex-1-yn-6-ylcarbonylthio, n-hex-2-yn-1-ylcarbonylthio, n-hex-2-yn-4-ylcarbonylthio, n-hex-2-yn-5-ylcarbonylthio, n-hex-2-yn-6-ylcarbonylthio, n-hex-3-yn-1-ylcarbonylthio, n-hex-3-yn-2-ylcarbonylthio, 3-methylpent-1-yn-1-ylcarbonylthio, 3-methylpent-1-yn-3-ylcarbonylthio, 3-methylpent-1-yn-4-ylcarbonylthio, 3-methylpent-1-yn-5-ylcarbonylthio, 4-methylpent-1-yn-1-ylcarbonylthio, 4-methylpent-2-yn-4-ylcarbonylthio or 4-methylpent-2-yn-5-ylcarbonylthio, in particular prop-2-yn-1-ylcarbonylthio;

($C_2$–$C_6$-alkynyl)carbonylthio such as: ethynylcarbonylthio or one of the radicals mentioned for ($C_3$–$C_6$-alkynyl)carbonylthio, in particular ethynylcarbonylthio or prop-2-yn-1-ylcarbonylthio;

($C_1$–$C_6$-alkoxy)carbonyl-$C_2$–$C_6$-alkenyl such as: $C_2$–$C_6$-alkenyl substituted by ($C_1$–$C_6$-alkoxy)carbonyl as mentioned above, i.e., for example, methoxycarbonylprop-2-en-1-yl;

$C_3$–$C_6$-alkenyloxy-$C_1$–$C_6$-alkyl such as: $C_1$–$C_6$-alkyl substituted by $C_3$–$C_6$-alkenyloxy as mentioned above, preferably allyloxy, 2-methylprop-2-en-1-yloxy, but-1-en-3-yloxy, but-1-en-4-yloxy or but-2-en-1-yloxy, i.e., for example, allyloxymethyl, 2-allyloxyethyl or but-1-en-4-yloxymethyl;

$C_3$–$C_6$-alkynyloxy-$C_1$–$C_6$-alkyl such as: $C_1$–$C_6$-alkyl substituted by $C_3$–$C_6$-alkynyloxy as mentioned above, preferably propargyloxy, but-1-yn-3-yloxy, but-1-yn-4-yloxy or but-2-yn-1-yloxy, i.e, for example, propargyloxymethyl or 2-propargyloxyethyl;

$C_3$–$C_8$-cycloalkyl such as: cyclopropyl, cyclobutyl, cyclopentyl, cyclohexyl, cycloheptyl or cyclooctyl, in particular cyclopentyl or cyclohexyl;

$C_3$–$C_8$-cycloalkyl-$C_1$–$C_4$-alkyl such as: cyclopropylmethyl, cyclobutylmethyl, cyclopentylmethyl, cyclohexylmethyl, cycloheptylmethyl, cyclooctylmethyl, 1-(cyclopropyl)ethyl, 1-(cyclobutyl)ethyl, 1-(cyclopentyl)ethyl, 1-(cyclohexyl)ethyl, 1-(cycloheptyl)ethyl, 1-(cyclooctyl)ethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclbbutyl)butyl, 4-(cyclopentyl)butyl, 4-(cyclohexyl)butyl, 4-(cycloheptyl)butyl or 4-(cyclooctyl)butyl, in particular cyclopentylmethyl or cyclohexylmethyl;

$C_3$–$C_6$-cycloalkyloxy such as: cyclopropyloxy, cyclobutyloxy, cyclopentyloxy or cyclohexyloxy;

$C_3$–$C_6$-cycloalkylthio such as: cyclopropylthio, cyclobutylthio, cyclopentylthio or cyclohexylthio;

$C_3$–$C_6$-cycloalkylcarbonyloxy such as: cyclopropylcarbonyloxy, cyclobutylcarbonyloxy, cyclopentylcarbonyloxy or cyclohexylcarbonyloxy;

$C_3$–$C_6$-cycloalkylsulfonyloxy such as: cyclopropylsulfonyloxy, cyclobutylsulfonyloxy, cyclopentylsulfonyloxy or cyclohexylsulfonyloxy;

$C_3$–$C_6$-cycloalkyloxy-$C_1$–$C_4$-alkyl such as: cyclopropyloxymethyl, cyclobutyloxymethyl, cyclopentyloxymethyl, cyclohexyloxymethyl, 1-(cyclopropyloxy)ethyl, 1-(cyclobutyloxy)ethyl, 1-(cyclopentyloxy)ethyl, 1-(cyclohexyloxy)ethyl, 2-(cyclopropyloxy)ethyl, 2-(cyclobutyloxy)ethyl, 2-(cyclopentyloxy)ethyl, 2-(cyclohexyloxy)ethyl, 3-(cyclopropyloxy)propyl, 3-(cyclobutyloxy)propyl, 3-(cyclopentyloxy)propyl, 3-(cyclohexyloxy)propyl, 4-(cyclopropyloxy)butyl, 4-(cyclobutyloxy)butyl, 4-(cyclopentyloxy)butyl or 4-(cyclohexyloxy)butyl, in particular cyclopentyloxymethyl, cyclohexyloxymethyl or 2-(cyclopentyloxy)ethyl;

$C_5$–$C_7$-cycloalkenyloxy such as: cyclopent-1-enyloxy, cyclopent-2-enyloxy, cyclopent-3-enyloxy, cyclohex-1-enyloxy, cyclohex-2-enyloxy, cyclohex-3-enyloxy, cyclohept-1-enyloxy, cyclohept-2-enyloxy, cyclohept-3-enyloxy or cyclohept-4-enyloxy;

$C_1$–$C_3$-alkylene such as: methylene, 1,2-ethylene or 1,3-propylene.

3- to 7-membered heterocyclyl, which may be linked directly or via an oxygen, alkoxy, alkenyloxy or alkynyloxy bridge, means both saturated, partially or completely unsaturated and aromatic heterocycles with one to three heteroatoms selected from a group consisting of one to three nitrogen atoms, one or two oxygen atoms and one or two sulfur atoms.

Examples of saturated heterocycles, which may contain a carbonyl or thiocarbonyl ring member, are:

oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl.

Examples of unsaturated heterocycles, which may contain a carbonyl or thiocarbonyl ring member, are:

dihydrofuran-2-yl, 1,2-oxazolin-3-yl, 1,2-oxazolin-5-yl, 1,3-oxazolin-2-yl.

5- and 6-membered heteroaromatic systems are preferred, i.e., for example, furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, also 2-pyrazinyl, 1,3,5-triazin-2-yl and 1,2,4-triazin-3-yl, in particular pyridyl, pyrimidyl, furanyl and thienyl.

All phenyl and heterocyclic rings are preferably unsubstituted or have one substituent.

Preferred C-organic radicals are methyl, ethyl, i- and n-propyl and butyl, in particular methyl and ethyl.

Surprisingly, the process of the invention results in a product which has a low viscosity and can easily be processed further.

In an advantageous embodiment of the process, the drying is carried out at temperatures in a range from 1 to 25, particularly preferably 3–20, ° C. above the melting point of the phenoxymethylbenzoic acids under the reaction conditions used (temperature, pressure). Under atmospheric pressure this leads to drying temperatures in the range from about 130 to 240° C.

The fact that the phenoxymethylbenzoic acids do not, despite the use of high temperatures above the melting point, undergo any decarboxylation or cleavage reactions was not to be expected beforehand either.

Another advantage of the process of the invention is that it can easily be implemented industrially because generally used standard reactors can be used; it is merely necessary to control the temperature accurately.

The process of the invention is preferably carried out in reactors with the possibility of thorough mixing, for example stirred reactors. The surface area of the liquid phase can be enlarged by circulation or stirring, which increases the effectiveness of the process of the invention.

It is also possible if necessary for the drying by the process of the invention to take place under inert conditions under protective gas if the stability of the phenoxymethylbenzoic acid to be dried makes this necessary.

It is possible by applying various degrees of vacuum to reduce the melting point of the phenoxymethylbenzoic acids employed and thus also the temperature at which the process of the invention is carried out, and thus to assist the drying. This may be advantageous in some cases.

If the phenoxymethylbenzoic acids employed contain water and solvents, and the boiling point of the solvent differs considerably from that of water, the drying can also be carried out in two stages, meaning that there is removal firstly of the lower-boiling component and then of the higher-boiling component. The two stages can for this purpose be achieved both by a temperature gradient and by a pressure gradient at constant temperature. It is, of course, also possible to change both the pressure and the temperature during the process. The only esssential point is that the phenoxymethylbenzoic acids to be dried do not leave the liquid state.

A multistage drying can be carried out both in one and in a plurality of reactors; when a multistage variant of the process is carried out continuously it is usually advantageous to carry it out in a plurality of reactors, each of which is operated under constant conditions. On the other hand, for a batchwise procedure it is easy to adjust a temperature or pressure gradient program in the range above or below-atmospheric pressure in one reactor.

The process is preferably carried out continuously.

The time taken to carry out the process of the invention is generally in the range from 1 min to 24 h, preferably from 1 min to 10 h. It depends inter alia on the drying temperature, the active surface area available for the drying, and the initial water and/or solvent content.

The energy input for melting the phenoxymethylbenzoic acids has proved to be less than expected because the heat of fusion of these compounds is very low. It is generally in the range from 50 to 400 kJ/kg.

The water- or solvent-wet phenoxymethylbenzoic acids can be prepared by processes known per se and described in the literature. Further details are therefore unnecessary here.

The water and/or solvent content of the phenoxymethylbenzoic acids before carrying out the process of the invention is usually in the range from 0.1 to 50, preferably from 5 to 30, % by weight. The water and/or solvent contents after carrying out the process of the invention are still in the range from 0.01 to 3, preferably from 0.01 to 2, % by weight.

If the phenoxymethylbenzoic acids to be dried still contain impurities whose boiling points are in the region of that of water or of the solvent present, the content thereof is likewise distinctly reduced by the process of the invention, and a purer product is obtained.

The phenoxymethylbenzoic acids obtainable by the process of the invention can very easily be processed further to fungicidal active substances. In the solidified state they have a distinctly reduced (virtually zero) tendency to agglutination and agglomeration and a distinctly reduced (virtually zero) tendency to consolidation through bridge formation.

EXAMPLES

General Procedure

In the following examples, the water-wet 2-(2-methylphenoxymethyl)benzoic acid was introduced in portions into a stirred reactor maintained at about 160° C. and containing, as holdup, about 10% of the introduced amount from a preceding batch. Depending on the amount to be introduced (batch size), the introduction took place over a period of from 1 to 13 h while stirring. The acid was also melted during this period. The resulting distillate was condensed. Completion of the addition was followed by stirring for one hour and then the purity and residual water content were determined on a homogeneous sample.

Example 1

660 g of a water-wet 2-(2-methylphenoxymethyl)benzoic acid with a water content of 9.6% by weight (63.6 g), a methanol content of 0.27% by weight (1.8 g) and a byproduct content of 2.5% by weight (16.5 g) were introduced into the melt reactor.

After an average residence time of 8 h at a temperature of 158 to 163° C. the melt was discharged and cooled. 595.1 g of a product were obtained with the following composition:

| | |
|---|---|
| 97.1% by weight (578.1 g) | of 2-(2-methylphenoxymethyl)benzoic acid |
| 0.087% by weight (0.52 g) | of water |
| 0.015% by weight (0.09 g) | of methanol |
| 2.77% by weight (16.5 g) | of byproducts |

Example 2

415.9 g of a water-wet 2-(2-methylphenoxymethyl)benzoic acid with a water content of 16.6% by weight (69.1 g), a methanol content of 0.12% by weight (0.5 g) and a byproduct content of 1.5% by weight (6.3 g) were introduced into the melt reactor.

After an average residence time of 8 h at a temperature of 158 to 165° C. the melt was discharged and cooled. 345.7 g of a product were obtained with the following composition:

| | |
|---|---|
| 96.1% by weight (339.0 g) | of 2-(2-methylphenoxymethyl)-benzoic acid |
| 0.03% by weight (0.11 g) | of water |
| 0.02% by weight (0.08 g) | of methanol |
| 1.9% by weight (6.5 g) | of byproducts |

Example 3

0.7 kg of a 2-(2-methylphenoxymethyl)benzoic acid containing about 10% by weight of methanol was washed 3 to 4 times with 200 ml of water each time to result in a residual methanol content of less than 1% by weight and was then dried.

633.2 g of this water-wet 2-(2-methylphenoxymethyl)benzoic acid with a water content of 3.8% by weight (24.2 g), a methanol content of 0.66% by weight (4.1 g) and a byproduct content of 2.0% by weight (12.9 g) were introduced into the melt reactor.

After an average residence time of 7 h at a temperature of 158 to 163° C. the melt was discharged and cooled. 606.3 g of a product were obtained with the following composition:

| | |
|---|---|
| 97.5% by weight (591.0 g) | of 2-(2-methylphenoxymethyl)benzoic acid |
| 0.052% by weight (0.32 g) | of water |
| 0.018% by weight (0.1 g) | of methanol |
| 2.48% by weight (14.9 g) | of byproducts |

We claim:

1. A process for drying phenoxymethylbenzoic acids of the general formula I

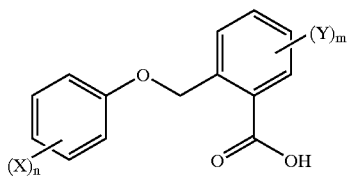

where X, Y, m and n have the following meanings:

X and Y are, independently, a halogen or a C-organic radical, m has a value from 0 to 4 and n has a value from 0 to 5 which comprises drying the water- and/or solvent-wet phenoxymethylbenzoic acids at a temperature in the range from 1° to 25° C. above their melting point under the drying conditions employed.

2. A process as claimed in claim 1, wherein the drying is carried out at temperatures in the range from 130° to 240° C. under atmospheric pressure.

3. A process as claimed in claim 1, wherein solvent residues are partly removed by washing with water before drying.

4. A process as claimed in claim 1, wherein a phenoxymethylbenzoic acid with a water and/or solvent content of from 0.1 to 50% by weight is employed.

* * * * *